(12) United States Patent
Prakash et al.

(10) Patent No.: US 9,301,803 B2
(45) Date of Patent: *Apr. 5, 2016

(54) SYSTEM AND METHOD FOR CHEMICALLY COOLING AN ABLATION ANTENNA

(71) Applicant: COVIDIEN LP, Mansfield, MA (US)

(72) Inventors: Mani N. Prakash, Boulder, CO (US); Kyle R. Rick, Boulder, CO (US); Francesca Rossetto, Longmont, CO (US)

(73) Assignee: Covidien LP, Mansfield, MA (US)

(\*) Notice: Subject to any disclaimer, the term of this patent is extended or adjusted under 35 U.S.C. 154(b) by 45 days.

This patent is subject to a terminal disclaimer.

(21) Appl. No.: 14/182,996

(22) Filed: Feb. 18, 2014

(65) Prior Publication Data

US 2014/0163545 A1    Jun. 12, 2014

Related U.S. Application Data

(63) Continuation of application No. 12/787,639, filed on May 26, 2010, now Pat. No. 8,652,127.

(51) Int. Cl.
*A61B 18/06* (2006.01)
*A61B 18/18* (2006.01)
*A61B 18/00* (2006.01)

(52) U.S. Cl.
CPC ... *A61B 18/1815* (2013.01); *A61B 2018/00023* (2013.01)

(58) Field of Classification Search
CPC .................. A61B 18/1815; A61B 2018/00023
USPC ........ 606/32, 34, 41; 607/101, 102, 105, 113, 607/114
See application file for complete search history.

(56) References Cited

U.S. PATENT DOCUMENTS

D263,020 S     2/1982  Rau, III
D295,893 S     5/1988  Sharkany et al.
(Continued)

FOREIGN PATENT DOCUMENTS

CN     1103807 A     6/1995
DE      390937 C     3/1924
(Continued)

OTHER PUBLICATIONS

Alexander et al., "Magnetic Resonance Image-Directed Stereotactic Neurosurgery: Use of Image Fusion with Computerized Tomography to EnhanceSpatial Accuracy" Journal Neurosurgery, 83 (1995), pp. 271-276.
(Continued)

*Primary Examiner* — Joseph Stoklosa
*Assistant Examiner* — Jocelyn D Ram

(57) ABSTRACT

A method of performing an ablation procedure includes the steps of inserting an antenna assembly into tissue and supplying energy thereto for application to tissue. The method also includes the step of causing contact between a first material and at least one other material disposed within the antenna assembly to thermally regulate the antenna assembly. According to another embodiment, an ablation system includes an energy delivery assembly. A first chamber is defined within the energy delivery assembly and is configured to hold a first chemical. Another chamber is defined within the energy delivery assembly and is configured to hold at least one other chemical. The first chamber and the other chamber are configured to selectively and fluidly communicate with each other to cause contact between the first chemical and the at least one other chemical to cause an endothermic reaction and/or an exothermic reaction.

20 Claims, 3 Drawing Sheets

(56) References Cited

U.S. PATENT DOCUMENTS

| | | |
|---|---|---|
| D295,894 S | 5/1988 | Sharkany et al. |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |
| D457,959 S | 5/2002 | Tetzlaff et al. |
| D496,997 S | 10/2004 | Dycus et al. |
| D499,181 S | 11/2004 | Dycus et al. |
| 6,824,555 B1* | 11/2004 | Towler et al. ............... 607/96 |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| 7,204,832 B2 | 4/2007 | Altshuler et al. |
| D541,938 S | 5/2007 | Kerr et al |
| 7,311,703 B2* | 12/2007 | Turovskiy et al. ............ 606/33 |
| D564,662 S | 3/2008 | Moses et al. |
| 7,642,451 B2* | 1/2010 | Bonn ............................ 174/28 |
| D613,412 S | 4/2010 | DeCarlo |
| 7,777,130 B2* | 8/2010 | Deborski et al. .......... 174/15.1 |
| 7,863,984 B1 | 1/2011 | Behnke |
| 7,875,024 B2 | 1/2011 | Turovskiy et al. |
| 7,963,785 B2 | 6/2011 | Arts et al. |
| 8,038,693 B2 | 10/2011 | Allen |
| 8,069,553 B2 | 12/2011 | Bonn |
| 8,093,500 B2* | 1/2012 | Deborski et al. ............... 174/92 |
| 8,118,808 B2 | 2/2012 | Smith et al. |
| 8,188,435 B2 | 5/2012 | Podhajsky et al. |
| 8,197,473 B2 | 6/2012 | Rossetto et al. |
| 8,202,270 B2 | 6/2012 | Rossetto et al. |
| 8,216,227 B2 | 7/2012 | Podhajsky |
| 8,235,981 B2 | 8/2012 | Prakash et al. |
| 8,282,632 B2 | 10/2012 | Rossetto |
| 8,292,880 B2* | 10/2012 | Prakash et al. ................ 606/33 |
| 8,292,881 B2 | 10/2012 | Brannan et al. |
| 8,313,486 B2 | 11/2012 | Kim et al. |
| 8,328,799 B2 | 12/2012 | Brannan |
| 8,328,800 B2 | 12/2012 | Brannan |
| 8,328,801 B2 | 12/2012 | Brannan |
| 8,334,812 B2 | 12/2012 | Brannan |
| 8,343,145 B2 | 1/2013 | Brannan |
| 8,353,903 B2 | 1/2013 | Podhajsky |
| 8,355,803 B2* | 1/2013 | Bonn ............................ 606/33 |
| 8,382,750 B2 | 2/2013 | Brannan |
| 8,394,087 B2 | 3/2013 | Willyard et al. |
| 8,394,092 B2 | 3/2013 | Brannan |
| 8,409,187 B2 | 4/2013 | Bonn |
| 8,409,188 B2 | 4/2013 | Kim et al. |
| 8,430,871 B2 | 4/2013 | Brannan |
| 8,652,127 B2 | 2/2014 | Prakash et al. |
| 2001/0029393 A1* | 10/2001 | Tierney et al. ................ 607/101 |
| 2005/0149010 A1* | 7/2005 | Turovskiy et al. ............ 606/33 |
| 2007/0287995 A1 | 12/2007 | Mayse |
| 2007/0299432 A1* | 12/2007 | Arless et al. ................. 606/21 |
| 2007/0299488 A1* | 12/2007 | Carr ............................... 607/101 |
| 2008/0147056 A1 | 6/2008 | van der Weide et al. |
| 2010/0256624 A1 | 10/2010 | Brannan et al. |
| 2010/0262134 A1 | 10/2010 | Jensen et al. |
| 2010/0268223 A1 | 10/2010 | Coe et al. |
| 2010/0268225 A1 | 10/2010 | Coe et al. |
| 2010/0286683 A1 | 11/2010 | Podhajsky |
| 2010/0305560 A1 | 12/2010 | Peterson |
| 2010/0321192 A1 | 12/2010 | Brannan |
| 2010/0331834 A1 | 12/2010 | Peterson et al. |
| 2011/0034919 A1 | 2/2011 | DeCarlo |
| 2011/0054458 A1 | 3/2011 | Behnke |
| 2011/0054459 A1 | 3/2011 | Peterson |
| 2011/0060326 A1 | 3/2011 | Smith et al. |
| 2011/0071511 A1 | 3/2011 | Brannan et al. |
| 2011/0071512 A1 | 3/2011 | Behnke, II et al. |
| 2011/0073594 A1 | 3/2011 | Bonn |
| 2011/0077633 A1 | 3/2011 | Bonn et al. |
| 2011/0077635 A1 | 3/2011 | Bonn |
| 2011/0077636 A1 | 3/2011 | Brannan et al. |
| 2011/0077637 A1 | 3/2011 | Brannan |
| 2011/0077638 A1 | 3/2011 | Brannan |
| 2011/0077639 A1 | 3/2011 | Brannan et al. |
| 2011/0098695 A1 | 4/2011 | Brannan |
| 2011/0118730 A1 | 5/2011 | DeCarlo |
| 2011/0118731 A1 | 5/2011 | Ladtkow |
| 2011/0152853 A1 | 6/2011 | Manley et al. |
| 2011/0172659 A1 | 7/2011 | Brannan |
| 2011/0184403 A1 | 7/2011 | Brannan |
| 2011/0190754 A1 | 8/2011 | Kim et al. |
| 2011/0196362 A1 | 8/2011 | Rossetto |
| 2011/0208177 A1 | 8/2011 | Brannan |
| 2011/0208180 A1 | 8/2011 | Brannan |
| 2011/0208184 A1 | 8/2011 | Brannan |
| 2011/0213351 A1 | 9/2011 | Lee et al. |
| 2011/0213352 A1 | 9/2011 | Lee et al. |
| 2011/0213353 A1 | 9/2011 | Lee et al. |
| 2011/0224504 A1 | 9/2011 | Ladtkow et al. |
| 2011/0238053 A1 | 9/2011 | Brannan et al. |
| 2011/0238055 A1 | 9/2011 | Kim et al. |
| 2011/0270240 A1 | 11/2011 | Shiu et al. |
| 2011/0282336 A1 | 11/2011 | Brannan et al. |
| 2011/0295245 A1 | 12/2011 | Willyard et al. |
| 2011/0295246 A1 | 12/2011 | Prakash et al. |
| 2011/0299719 A1 | 12/2011 | Podhajsky et al. |
| 2011/0301589 A1 | 12/2011 | Podhajsky et al. |
| 2011/0301590 A1 | 12/2011 | Podhajsky et al. |
| 2011/0301591 A1 | 12/2011 | Podhajsky et al. |
| 2011/0319880 A1 | 12/2011 | Prakash et al. |
| 2012/0004651 A1 | 1/2012 | Shiu et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |

(56) References Cited

FOREIGN PATENT DOCUMENTS

| | | |
|---|---|---|
| EP | 0 836 868 A2 | 4/1998 |
| EP | 0 882 955 A1 | 12/1998 |
| EP | 1 159 926 A2 | 12/2001 |
| EP | 1977709 A1 | 10/2008 |
| EP | 1977710 A1 | 10/2008 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| JP | 2001231870 A | 8/2001 |
| JP | 2008142467 A | 6/2008 |
| SU | 166452 | 11/1964 |
| SU | 401367 A1 | 10/1973 |
| SU | 727201 A2 | 4/1980 |
| WO | 2005/011049 A2 | 2/2005 |
| WO | 2007/006158 A1 | 1/2007 |
| WO | 2007112081 A1 | 10/2007 |
| WO | 2010/035831 A1 | 4/2010 |

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic .RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., Theoretical Aspects of "Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.

(56) References Cited

OTHER PUBLICATIONS

Humphries Jr. et al., "Finite.cndot.Element Codes to Model Electrical Heating and Non.cndot.Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences. cndot. Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis.TM. Technology (Date Unknown). "Overcoming the Challenge" located at: <http://www.urologix.com!medicaUtechnology.html> last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.

(56) References Cited

OTHER PUBLICATIONS

ValleyLab Brochure, "Electosurgery: A Historical Overview", Innovations in Electrosurgery, 1999.
Vallfors et al., "Automatically Controlled Bipolar Electrocoagulation:'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.

(56) References Cited

OTHER PUBLICATIONS

European Search Report EP 09173268.5 extended dated Jan. 27, 2010.
European Search Report EP 10158944.8 extended dated Jun. 21, 2010.
European Search Report EP 10161722.3 extended dated Jun. 16, 2010.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 08/136,098, filed Oct. 14, 1993, Stern.

* cited by examiner

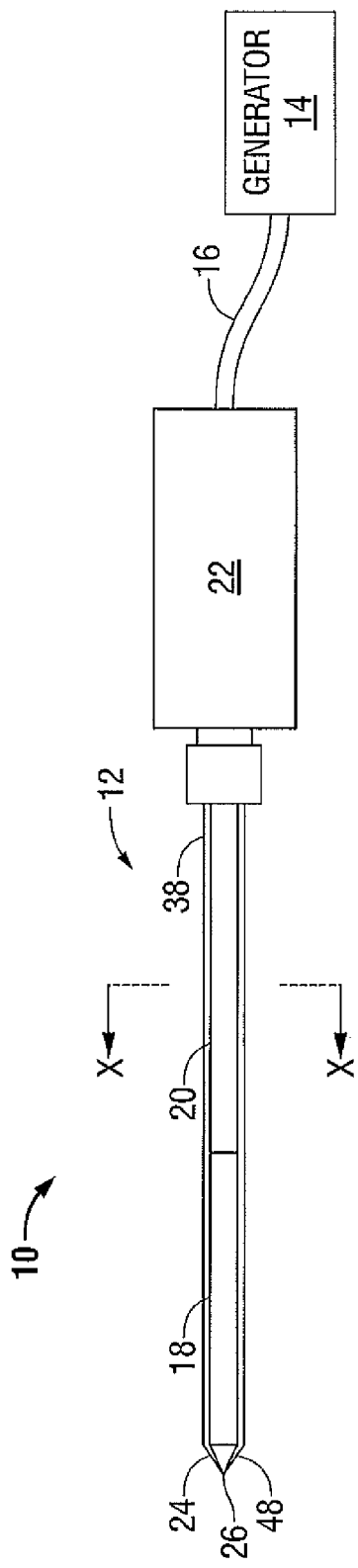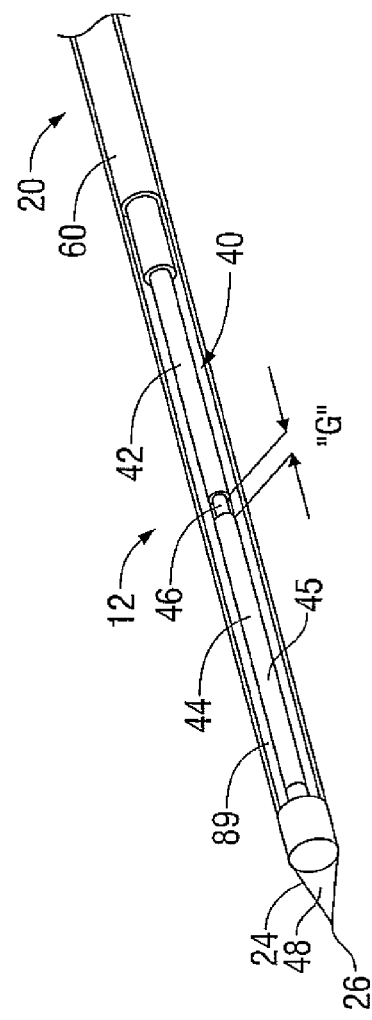

SYSTEM AND METHOD FOR CHEMICALLY COOLING AN ABLATION ANTENNA

CROSS-REFERENCE TO RELATED APPLICATIONS

The present application is a continuation application of U.S. patent application Ser. No. 12/787,639, filed on May 26, 2010, the entire contents of which are incorporated by reference herein.

BACKGROUND

1. Technical Field

The present disclosure relates generally to microwave antennas used in tissue ablation procedures. More particularly, the present disclosure is directed to a microwave antenna having a coolant assembly for chemically cooling the microwave antenna.

2. Background of Related Art

In the treatment of diseases such as cancer, certain types of cancer cells have been found to denature at elevated temperatures which are slightly lower than temperatures normally injurious to healthy cells. These types of treatments, known generally as hyperthermia therapy, typically utilize electromagnetic radiation to heat diseased cells to temperatures above 41° Celsius while maintaining adjacent healthy cells at lower temperatures where irreversible cell destruction will not occur. Other procedures utilizing electromagnetic radiation to heat tissue also include ablation and coagulation of the tissue. Such ablation procedures, e.g., such as those performed for menorrhagia, are typically done to ablate and coagulate the targeted tissue to denature or kill the tissue. Many procedures and types of devices utilizing electromagnetic radiation therapy are known in the art. Such therapy is typically used in the treatment of tissue and organs such as the prostate, heart, kidney, lung, brain, and liver.

Presently, there are several types of microwave probes in use, e.g., monopole, dipole, and helical, which may be inserted into a patient for the treatment of tumors by heating the tissue for a period of time sufficient to cause cell death and necrosis in the tissue region of interest. Such microwave probes may be advanced into the patient, e.g., laparoscopically or percutaneously, and into or adjacent to the tumor to be treated. The probe is sometimes surrounded by a dielectric sleeve.

However, in transmitting the microwave energy into the tissue, the outer surface of the microwave antenna typically heats up and may unnecessarily effect healthy tissue immediately adjacent the antenna outer surface. This creates a water or tissue phase transition (steam) that allows the creation of a significant additional heat transfer mechanism as the steam escapes from the local/active heating area and re-condenses further from the antenna. The condensation back to water deposits significant energy further from the antenna/active treatment site. This local tissue desiccation occurs rapidly resulting in an antenna impedance mismatch that both limits power delivery to the antenna and effectively eliminates steam production/phase transition as a heat transfer mechanism for tissue ablation.

To prevent the unintended effects on adjacent tissue, several different cooling methodologies are conventionally employed. For instance, some microwave antennas utilize balloons that are inflatable around selective portions of the antenna to cool the surrounding tissue. Thus, the complications associated with unintended tissue effects by the application of microwave radiation to the region are minimized. Typically, the cooling system and the tissue are maintained in contact to ensure adequate cooling of the tissue.

Other devices attempt to limit the heating of tissue adjacent the antenna by selectively blocking the propagation of the microwave field generated by the antenna. These cooling systems also protect surrounding healthy tissues by selectively absorbing microwave radiation and minimizing thermal damage to the tissue by absorbing heat energy.

SUMMARY

According to an embodiment of the present disclosure, a method of performing an ablation procedure includes the steps of inserting an antenna assembly into tissue and supplying energy to the antenna assembly for application to tissue. The method also includes the step of causing contact between a first material and at least one other material disposed within the antenna assembly to thermally regulate the antenna assembly.

According to another embodiment of the present disclosure, a method of performing an ablation procedure includes the steps of inserting an antenna assembly into tissue and supplying energy to the antenna assembly for application to tissue. The method also includes the steps of causing contact between a first chemical held within a first chamber defined within the antenna assembly and at least one other chemical disposed within at least one other chamber defined within the antenna assembly to cause one of an endothermic reaction and an exothermic reaction to thermally regulate the antenna assembly.

According to another embodiment of the present disclosure, an ablation system includes an energy delivery assembly configured to deliver energy from a power source to tissue. A first chamber is defined within the energy delivery assembly and is configured to hold a first chemical. At least one other chamber is defined within the energy delivery assembly and is configured to hold at least one other chemical. The first chamber and the at least one other chamber are configured to selectively and fluidly communicate with each other to cause contact between the first chemical and the at least one other chemical to cause one of an endothermic reaction and an exothermic reaction to thermally regulate the energy delivery assembly.

BRIEF DESCRIPTION OF THE DRAWINGS

The above and other aspects, features, and advantages of the present disclosure will become more apparent in light of the following detailed description when taken in conjunction with the accompanying drawings in which:

FIG. 1 is a schematic diagram of the microwave ablation system according to an embodiment of the present disclosure;

FIG. 2 is a perspective, internal view of a microwave antenna assembly taken along line X-X according to an embodiment of the present disclosure;

DETAILED DESCRIPTION

Figure 3A:
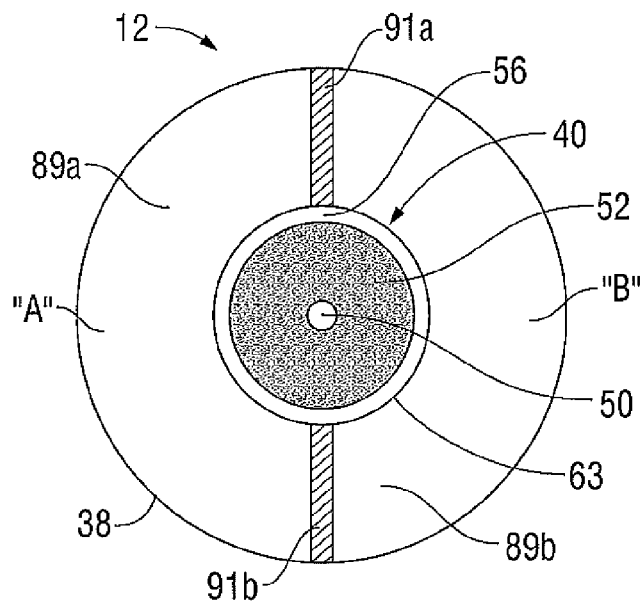
FIGS. 3A and 3B are cross-sectional views taken along line X-X of the microwave antenna assembly of FIG. 1 according to various embodiments of the present disclosure.

Embodiments of the presently disclosed apparatus are described in detail below with reference to the drawings wherein like reference numerals identify similar or identical elements in each of the several views. In the discussion that follows, the term "proximal" will refer to the portion of a structure that is closer to a user, while the term "distal" will refer to the portion of the structure that is farther from the user.

Generally, the present disclosure is directed to a microwave antenna assembly having an energy source or generator adapted to deliver energy to tissue via the antenna assembly. The antenna assembly includes one or more chambers configured to receive and accommodate suitable chemicals (e.g., fluid, solid, a fluid and solid combination) therein that, upon mutual contact, mixture, dissolving, or reaction with each other, cause either an endothermic reaction or exothermic reaction depending on the chemicals used. Two or more chemicals are disposed within individual sealed chambers disposed within the antenna assembly. Through use of various methods of the various embodiments of the present disclosure, the chemicals are caused to contact each other at the appropriate time (e.g., during a tissue ablation procedure), thereby causing an endothermic or exothermic reaction, depending on the chemicals used. For example, the individual chambers holding the chemicals may be separated by a breakable membrane. In this scenario, the antenna assembly may be semi-flexible or semi-rigid such that the antenna assembly may be flexed or bent at the appropriate time to cause the membrane to break, thereby allowing the previously separated chemicals to contact each other and cause either an endothermic or exothermic reaction. Additionally or alternatively, the individual sub-chambers holding the chemicals may be separated by a mechanical interface configured to selectively cause communication between the sub-chambers through use of an actuation interface disposed on the antenna assembly.

Embodiments of the present disclosure may also be implemented using a microwave monopolar antenna or other suitable electrosurgical devices such as, for example, radiofrequency monopolar and/or bipolar electrodes, an ultrasound transducer, laser fiber, a direct current (DC) heating element, or the like, and may be implemented in operable cooperation with any suitable energy source (e.g., radiofrequency, direct current, microwave, laser, ultrasound, etc.).

In the scenario wherein an endothermic reaction results from contact between the two or more chemicals, the antenna assembly and/or surrounding tissue is cooled by the endothermic reaction. In use, while the antenna assembly is placed relative to the desired tissue site, the heat generated by the application of microwave energy from the antenna assembly to tissue may be cooled by causing an endothermic reaction within the antenna assembly. In the scenario wherein an exothermic reaction results from contact between the two or more chemicals, the antenna assembly and/or surrounding tissue is heated by the exothermic reaction. In use, while the antenna assembly is placed relative to the desired tissue site, surrounding tissue such as, for example, the insertion tract resulting from the insertion of the antenna assembly or an introducer into the tissue, may be heated or cauterized to stop bleeding or prevent tumor cells from "seeding" the insertion tract.

FIG. 1 shows a microwave ablation system 10 that includes a microwave antenna assembly 12 coupled to a microwave generator 14 via a flexible coaxial cable 16. The generator 14 is configured to provide microwave energy at an operational frequency from about 300 MHz to about 3000 MHz, although other suitable frequencies are also contemplated.

In the illustrated embodiment, the antenna assembly 12 includes a radiating portion 18 connected by feedline 20 (or shaft) to the cable 16. More specifically, the antenna assembly 12 is coupled to the cable 16 through a connection hub or handle 22 that is connected in fluid communication with a sheath 38. The sheath 38 encloses radiating portion 18 and feedline 20 to form a chamber 89 (FIG. 2) allowing one or more materials such as, for example, fluid, gas, coolant, chemicals, saline, water, powdered solids, or any combination thereof, to circulate within and/or occupy space within chamber 89. In some embodiments, connection hub 22 may be coupled to a suitable supply pump (not shown) adapted to supply fluid or coolant to chamber 89. In some embodiments, antenna assembly 12 may be embodied as, for example without limitation, a radiofrequency monopolar and/or bipolar electrode assembly, an ultrasound transducer, laser fiber, a direct current (DC) heating element, or the like.

FIG. 2 illustrates a perspective view taken along line X-X of FIG. 1 showing the radiating portion 18 of the antenna assembly 12 according to one embodiment of the present disclosure having a dipole antenna 40. The dipole antenna 40 is coupled to the feedline 20 that electrically connects antenna assembly 12 to the generator 14. The dipole antenna 40 includes a proximal portion 42 and a distal portion 44 interconnected at a feed point 46. The distal portion 44 and the proximal portion 42 may be either balanced (e.g., of equal lengths) or unbalanced (e.g., of unequal lengths). A dipole feed gap "G" is disposed between the proximal and distal portions 42 and 44 at the feed point 46. The gap "G" may be from about 1 nun to about 3 mm. In one embodiment, the gap "G" may thereafter be filled with a dielectric material at the feed point 46. The dielectric material may be polytetrafluoroethylene (PTFE), such as Teflon® sold by DuPont of Willmington, Del. In another embodiment, the gap "G" may be coated with a dielectric seal coating.

With continued reference to FIG. 2, the antenna assembly 12 also includes a choke 60 disposed around the feedline 20. The choke 60 may be a quarter-wavelength shorted choke that is shorted to the feedline 20 at the proximal end (not illustrated) of the choke 60 by soldering or other suitable methods.

Assembly 12 also includes a tip 48 having a tapered end 24 that terminates, in one embodiment, at a pointed end 26 to allow for insertion into tissue with minimal resistance at a distal end of the radiating portion 18. In those cases where the radiating portion 18 is inserted into a pre-existing opening, tip 48 may be rounded or flat. The tip 48 may be formed from a variety of heat-resistant materials suitable for penetrating tissue, such as metals (e.g., stainless steel) and various thermoplastic materials, such as poletherimide, and polyamide thermoplastic resins.

Figure 3B:
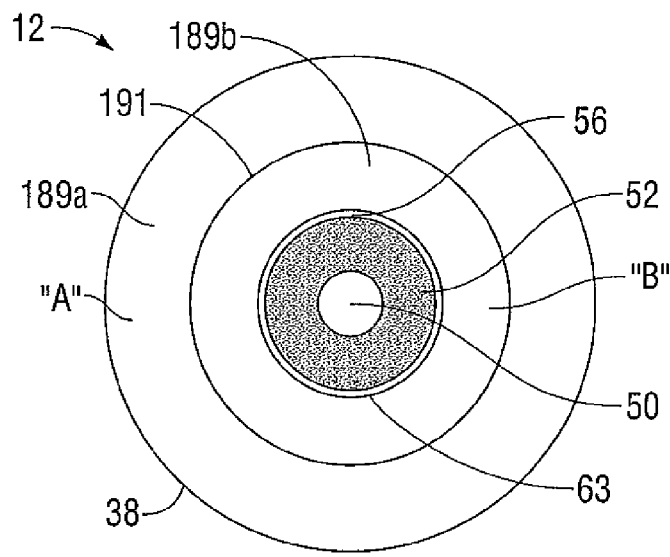

FIGS. 3A and 3B illustrate cross-sectional views of antenna assembly 12 taken along line X-X of FIG. 1 according to various embodiment of the present disclosure. As shown by the illustrated embodiments, at least a portion of the feedline 20 and/or the radiating portion 18 may be formed from a semi-rigid and/or semi-flexible structure (e.g., coaxial cable) and includes an inner conductor 50 (e.g., wire) surrounded by an inner insulator 52 with suitable dielectric properties. The inner insulator 52 is, in turn, surrounded by an outer conductor 56 (e.g., cylindrical conducting sheath). The inner and outer conductors 50 and 56, respectively, may be constructed of copper, gold, stainless steel or other conductive metals with similar conductivity values. The metals may be plated with other materials, e.g., other conductive materials, to improve their properties, e.g., to improve conductivity or decrease energy loss, etc.

Since the radiating portion 18 and the feedline 20 are in direct contact with materials such as fluid and/or solid, these components of the assembly 12 are sealed by a protective sleeve 63 (FIGS. 3A and 3B) to prevent any fluid seeping therein. This may be accomplished by applying any type of melt-processible polymers using conventional injection molding and screw extrusion techniques. In one embodiment, a sleeve of fluorinated ethylene propylene (FEP) shrink wrap may be applied to the entire assembly 12, namely the feedline 20 and the radiating portion 18. The protective sleeve 63 is then heated to seal the feedline 20 and radiating portion 18. The protective sleeve 63 prevents any material from penetrating into the assembly 12.

Referring specifically now to FIG. 3A, one embodiment of the present disclosure is shown and includes separation members 91a, 91b disposed transversely between protective sleeve 63 and an inner surface of sheath 38 along at least a longitudinal portion of chamber 89 to sub-divide chamber 89 into semi-circular sub-chambers 89a and 89b. Sub-chambers 89a and 89b are configured to retain first and second chemicals "A" and "B", respectively, therein. Separation members 91a, 91b are configured to hold chemicals "A" and "B" within sub-chambers 89a and 89b, respectively, in a seal-tight manner such that chemicals "A" and "B" are selectively prevented from contacting each other until needed to contact each other.

Figure 3C:
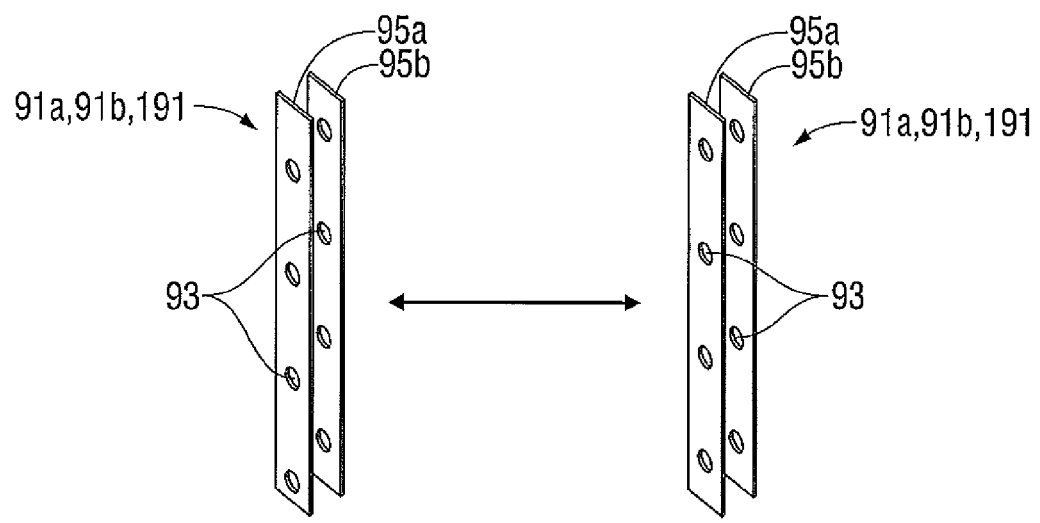
FIG. 3C is a perspective view of a component detailing operation of the microwave antenna assembly of either FIGS. 3A and 3B.

In one embodiment, separation members 91a, 91b may be slidable or movable, as discussed in further detail below with reference to FIG. 3C. In another embodiment, separation members 91a, 91b are formed of a breakable material, such as a breakable membrane, the structural integrity of which is compromised upon the application of a sufficient force mechanically, electrically, or electro-mechanically thereto (e.g., bending of semi-rigid feedline 20). In this scenario, once the separation members 91a, 91b are broken or ruptured, contact between chemicals "A" and "B" is facilitated and, depending on the identity of chemicals "A" and/or "B", an endothermic or exothermic reaction ensues to cool or heat the antenna assembly 12, respectively.

Chemical pairs used to generate an endothermic reaction through contact, reaction, dissolving, or mixture may include, without limitation, barium hydroxide octahydrate crystals with dry ammonium chloride, ammonium chloride with water, thionyl chloride ($SOCl_2$) with cobalt(II) sulfate heptahydrate, water with ammonium nitrate, water with potassium chloride, and ethanoic acid with sodium carbonate. Chemical pairs used to generate an exothermic reaction may include, without limitation, concentrated acid with water, water with anhydrous copper(II) sulfate, water with calcium chloride ($CaCl_2$), alkalis with acids, acids with bases, etc.

Referring specifically now to FIG. 3B, another embodiment of the present disclosure includes a concentric separation member 191 disposed longitudinally through at least a portion of a cross-section of chamber 89 to subdivide chamber 89 into longitudinal sub-chambers 189a and 189b. Separation member 191 is substantially as described above with respect to separation members 91a, 91b of FIG. 3A and will only be described to the extent necessary to describe the differences between the embodiments of FIGS. 3A and 3B. Similar to separation members 91a, 91b described above with respect to FIG. 3A, sub-chambers 189a and 189b are configured to hold chemicals "A" and "B" therein. Separation member 191 may be slidable or movable, as discussed in further detail below with reference to FIG. 3C. In another embodiment, separation member 191 is formed of a breakable material, such as a breakable membrane, the structural integrity of which is compromised upon the application of a sufficient force mechanically, electrically, or electro-mechanically thereto (e.g., bending of semi-rigid feedline 20). In this scenario, once separation member 191 is broken, contact between chemicals "A" and "B" is facilitated and, depending on the identity of chemicals "A" and/or "B", an endothermic or exothermic reaction ensues to cool or heat the antenna assembly 12, respectively.

For purposes of simplifying the description of FIG. 3C to follow, FIG. 3C will be described below with respect to the embodiment of FIG. 3B. However, the following description may also apply to the operation of the embodiment of FIG. 3A and, as such, any reference to separation member 191 or sub-chambers 89a and 89b throughout the following description may be substituted with reference to separation members 91a, 91b and sub-chambers 89a, 89b, respectively.

Separation member 191 may, in certain embodiments, be configured to be moved, actuated, slid, or the like, to permit or prevent communication between sub-chambers 189a and 189b, respectively, such that contact between chemicals "A" and "B" is selectively facilitated or prevented. More specifically, separation member 191 includes a pair of interfacing surfaces 95a and 95b that each include a plurality of apertures 93. As illustrated by FIG. 3C, separation member 191 may be actuated such that interfacing surfaces 95a and 95b move relative to each other or, alternatively, such that one surface (e.g., 95a) moves relative to a stationary surface (e.g., 95b). In either scenario, movement of surface 95a and/or surface 95b operates to bring apertures 93 of both surfaces 95a, 95b into and out of alignment with each other. That is, when apertures 93 of surface 95a are brought into substantial alignment with corresponding apertures 93 of surface 95b, sub-chambers 189a and 189b are in communication via apertures 93 such that contact between chemicals "A" and "B" is facilitated, Likewise, when apertures 93 of surface 95a are brought out of substantial alignment with apertures 93 of surface 95b, communication between sub-chambers 189a and 189b is prevented.

Actuation of separation member 191 may be facilitated by an actuation member (not shown) disposed on the exterior of the antenna assembly 12 at a location suitable for operation by a user during an ablation procedure (e.g., the connection hub 22). The actuation member, in this scenario, is operably coupled to separation member 191 by any suitable number of configurations, components, mechanical connections, and/or components (e.g., gears, links, springs, rods, etc.), and/or electro-mechanical connections, configurations, and/or components such that separation member 191 may operate as intended. The actuation member may be embodied as, for example without limitation, a button, slide button, knob, lever, or the like. For example, in the scenario wherein the actuation member is a slide button, the slide button may be configured to slide longitudinally along the exterior of the antenna assembly 12 (e.g., along the connection hub 22) to actuate separation members 91a, 91b or separation member 191.

Referring to FIGS. 3A and 3B, the depiction of sub-chambers 89a, 89b and 189a, 189b is illustrative only in that antenna assembly 12 may include a plurality of sub-chambers, each of which is configured to hold a chemical therein. In this scenario, an endothermic or exothermic reaction may be caused by the contact, mixture, dissolving, or reaction between three or more chemicals to thermally regulate the antenna assembly 12.

Figure 4:
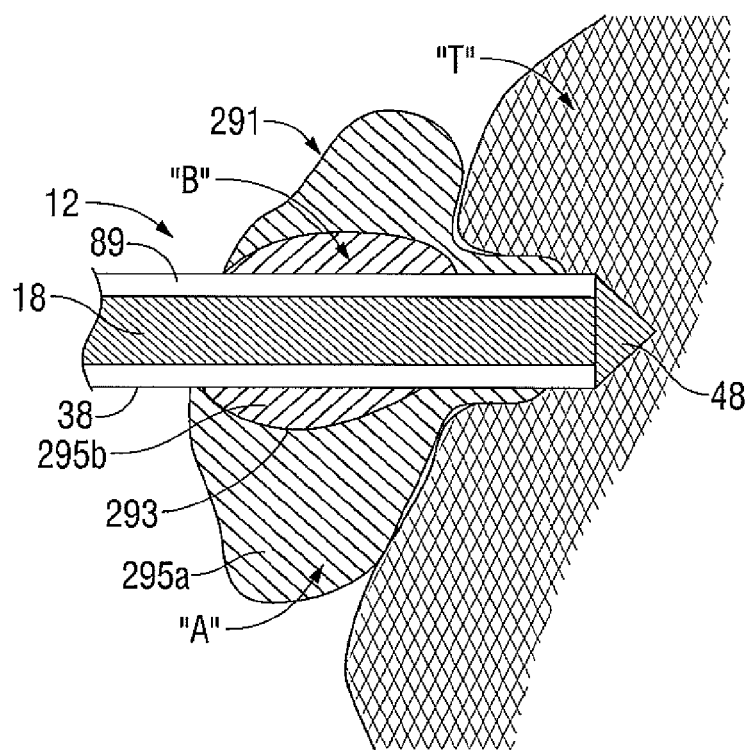
FIG. 4 is a cross-sectional view of a microwave antenna assembly inserted into tissue according to another embodiment of the present disclosure.

Referring now to FIG. 4, another embodiment of antenna assembly 12 is shown and includes a flexible sheath 291 disposed on at least a portion of the sheath 38 enclosing radiating portion 18 and feedline 20. Flexible sheath 291 includes an outer sub-chamber 295a configured to hold chemical "A" and an inner sub-chamber 295b configured to hold chemical "B". Outer sub-chamber 295a surrounds inner sub-chamber 295b and is separated therefrom at least partially by a breakable membrane 293 (e.g., a shared surface between outer sub-chamber 295a and inner sub-chamber 295b). Upon insertion of antenna assembly 12 into tissue "T", as illustrated in FIG. 4, outer sub-chamber 295a is configured to conform to the surface of antenna assembly 12 along a portion thereof inserted through tissue "T" and disposed within the insertion tract. Along the portion of antenna assembly 12 exterior to the tissue "T" or outside the insertion tract, outer sub-chamber 295a conforms to the surface of tissue "T" (e.g., the patient's skin, a target organ, etc.).

In use, once antenna assembly 12 is inserted into tissue "T", the structural integrity of membrane 293 may be compromised to cause communication between outer and inner sub-chambers 295a and 295b and facilitate contact between chemicals "A" and "B". As discussed hereinabove, contact between materials "A" and "B" causes an endothermic or exothermic reaction depending on the identity of materials "A" and/or "B". In the scenario wherein an exothermic reaction results, for example, the antenna assembly 12 may be heated sufficient to thermally modify tissue in the insertion tract to stop bleeding upon removal of antenna assembly 12 from tissue "T". An exothermic reaction may also be used to simply heat the antenna assembly 12 if the antenna assembly 12 becomes too cold. In the scenario wherein an endothermic reaction results, for example, the antenna assembly 12 may be cooled sufficient to cool the insertion tract and stop bleeding upon removal of antenna assembly 12 from tissue "T". An endothermic reaction may also be used to cool the surface of the tissue "T" facilitated by the conforming of outer sub-chamber 295a to the surface of the tissue "T" as described hereinabove. An endothermic reaction may also be used to simply cool the antenna assembly 12 if the antenna assembly 12 becomes too hot.

The above-discussed system provides for the generation of endothermic and exothermic reactions within antenna assembly 12. The endothermic reaction removes the heat generated by the antenna assembly 12. By keeping the antenna assembly 12 and/or the ablation zone cooled, there is significantly less sticking of tissue to the antenna assembly 12. In addition, the endothermic reaction acts as a buffer for the assembly 12 and prevents near field dielectric properties of the assembly 12 from changing due to varying tissue dielectric properties. For example, as microwave energy is applied during ablation, desiccation of the tissue around the radiating portion 18 results in a drop in tissue complex permittivity by a considerable factor (e.g., about 10 times). The dielectric constant (er') drop increases the wavelength of microwave energy in the tissue, which affects the impedance of un-buffered microwave antenna assemblies, thereby mismatching the antenna assemblies from the system impedance (e.g., impedance of the cable 16 and the generator 14). The increase in wavelength also results in a power dissipation zone which is much longer in length along the assembly 12 than in cross sectional diameter. The decrease in tissue conductivity (er") also affects the real part of the impedance of the assembly 12. The fluid dielectric buffering according to the present disclosure also moderates the increase in wavelength of the delivered energy and drop in conductivity of the near field, thereby reducing the change in impedance of the assembly 12, allowing for a more consistent antenna-to-system impedance match and spherical power dissipation zone despite tissue behavior.

The described embodiments of the present disclosure are intended to be illustrative rather than restrictive, and are not intended to represent every embodiment of the present disclosure. Embodiments of the present disclosure may also be implemented in a microwave monopolar antenna or other suitable electrosurgical devices (monopolar or bipolar) and may be applied with any suitable energy source (e.g., radiofrequency, direct current, microwave, laser, ultrasound, etc.) where, for example, reduction of heat and/or an increase in localized heating is desired. Various modifications and variations can be made without departing from the spirit or scope of the disclosure as set forth in the following claims both literally and in equivalents recognized in law.

What is claimed is:

1. An energy-delivery assembly configured to deliver energy from an energy source to tissue, the energy-delivery assembly comprising:
    a radiating portion;
    a flexible sheath disposed over at least a portion of the radiating portion, the flexible sheath defining an outer chamber and an inner chamber disposed within the outer chamber, wherein a distal end of the outer chamber extends past a distal end of the inner chamber; and
    a first composition disposed within the outer chamber and a second composition disposed within the inner chamber, wherein the outer chamber and the inner chamber are configured to selectively and fluidly communicate with each other to cause contact between the first composition and the second composition to cause one of an endothermic reaction or an exothermic reaction.

2. The energy-delivery assembly according to claim 1, wherein the outer chamber is separated from the inner chamber by a selectively rupturable membrane configured to break upon an application of at least one of a mechanical, electro-mechanical, or electrical force.

3. The energy-delivery assembly according to claim 1, further comprising a protective sleeve wrapped around the radiating portion.

4. The energy-delivery assembly according to claim 3, wherein the protective sleeve includes fluorinated ethylene propylene shrink wrap.

5. The energy-delivery assembly according to claim 1, further comprising a coolant sheath enclosing the radiating portion to define a space forming a coolant chamber.

6. The energy-delivery assembly according to claim 5, further comprising a third composition disposed in the coolant chamber.

7. The energy-delivery assembly according to claim 6, wherein the third composition is selected from the group consisting of a coolant, saline and water.

8. The energy-delivery assembly according to claim 1, wherein the first composition is selected from the group consisting of barium hydroxide octahydrate, ammonium chloride, thionyl chloride, water and ethanoic acid.

9. The energy-delivery assembly according to claim 1, wherein the second composition is selected from the group consisting of ammonium chloride, water, cobalt sulfate heptahydrate, ammonium nitrate, potassium chloride, sodium carbonate, anhydrous copper sulfate, and calcium chloride.

10. The energy-delivery assembly according to claim 1, further comprising a feedline electrically coupled to the radiating portion.

11. An energy-delivery assembly configured to deliver energy from an energy source to tissue, the energy-delivery assembly comprising:
    a radiating portion;
    an outer jacket enclosing the radiating portion to define a coolant chamber;
    a flexible sheath disposed over at least a portion of the outer jacket, the flexible sheath defining an outer chamber and an inner chamber disposed within the outer chamber, wherein a distal end of the outer chamber extends past a distal end of the inner chamber; and a first composition disposed within the outer chamber and a second composition disposed within the inner chamber, wherein the outer chamber and the inner chamber are configured to selectively and fluidly communicate with each other to cause contact between the first composition and the second composition to cause one of an endothermic reaction or an exothermic reaction.

12. The energy-delivery assembly according to claim 11, wherein the outer chamber is separated from the inner chamber by a selectively rupturable membrane configured to rupture upon an application of at least one of a mechanical, electro-mechanical, or electrical force.

13. The energy-delivery assembly according to claim 11, further comprising a protective sleeve wrapped around the radiating portion.

14. The energy-delivery assembly according to claim 13, wherein the protective sleeve includes fluorinated ethylene propylene shrink wrap.

15. The energy-delivery assembly according to claim 11, wherein the first composition is selected from the group consisting of barium hydroxide octahydrate, ammonium chloride, thionyl chloride, water and ethanoic acid.

16. The energy-delivery assembly according to claim 11, wherein the second composition is selected from the group consisting of ammonium chloride, water, cobalt sulfate heptahydrate, ammonium nitrate, potassium chloride, sodium carbonate, anhydrous copper sulfate, and calcium chloride.

17. The energy-delivery assembly according to claim 11, further comprising a third composition disposed in the coolant chamber.

18. The energy-delivery assembly according to claim 17, wherein the third composition is selected from the group consisting of a coolant, saline, and water.

19. The energy-delivery assembly according to claim 11, further comprising a feedline electrically coupled to the radiating portion.

20. The energy-delivery assembly according to claim 19, wherein the outer jacket encloses the feedline.

\* \* \* \* \*